US008968665B2

(12) United States Patent
Allison

(10) Patent No.: US 8,968,665 B2
(45) Date of Patent: Mar. 3, 2015

(54) CANDLES CAPABLE OF DIFFUSING A PLURALITY OF ACTIVE VOLATILE SUBSTANCES SIMULTANEOUSLY

(75) Inventor: Gerald Allison, East Windsor, NJ (US)

(73) Assignee: Firmenich SA, Geneva (CH)

( * ) Notice: Subject to any disclaimer, the term of this patent is extended or adjusted under 35 U.S.C. 154(b) by 47 days.

(21) Appl. No.: 13/878,928

(22) PCT Filed: Oct. 7, 2011

(86) PCT No.: PCT/EP2011/067540
§ 371 (c)(1),
(2), (4) Date: Apr. 11, 2013

(87) PCT Pub. No.: WO2012/049084
PCT Pub. Date: Apr. 19, 2012

(65) Prior Publication Data

US 2013/0216428 A1 Aug. 22, 2013

Related U.S. Application Data

(60) Provisional application No. 61/392,690, filed on Oct. 13, 2010.

(51) Int. Cl.

| | |
|---|---|
| ***A61L 9/00*** | (2006.01) |
| ***A62B 7/08*** | (2006.01) |
| ***F23Q 2/32*** | (2006.01) |
| ***F23D 3/16*** | (2006.01) |
| ***A24F 25/00*** | (2006.01) |
| ***C11C 5/00*** | (2006.01) |
| ***C11C 5/02*** | (2006.01) |

(52) U.S. Cl.
CPC ................ *C11C 5/002* (2013.01); *C11C 5/008* (2013.01); *C11C 5/02* (2013.01)
USPC ............... 422/126; 422/5; 422/123; 422/306; 239/34; 431/126; 431/288; 431/289

(58) Field of Classification Search
CPC ............ A61L 9/00; A61L 9/03; A61L 9/037; A61L 9/12; A61L 9/127
USPC ............. 422/1, 5, 28, 123, 126, 306; 239/34; 431/126, 288–289
See application file for complete search history.

(56) References Cited

U.S. PATENT DOCUMENTS

| | | | | |
|---|---|---|---|---|
| 3,744,956 | A | 7/1973 | Hess | |
| 2005/0163649 | A1 | 7/2005 | Friedrich | |
| 2007/0003895 | A1 * | 1/2007 | Conover | 431/289 |

FOREIGN PATENT DOCUMENTS

| | | | |
|---|---|---|---|
| DE | 36 40 644 A1 | 6/1988 | |
| EP | 1749080 | 3/2012 | |
| WO | WO 2008/016867 A2 | 2/2008 | |

* cited by examiner

*Primary Examiner* — Monzer R Chorbaji
(74) *Attorney, Agent, or Firm* — Winston & Strawn LLP

(57) ABSTRACT

The present invention relates to candles capable of diffusing a plurality of volatile active substances simultaneously, a base portion, at least one wick and a plurality of cartridges carrying the volatile active substances to be diffused, the base portion being provided with a plurality of holes adapted to receive the cartridges. The invention further relates to a method for diffusing a plurality of active substances simultaneously comprising manufacturing and burning such candle.

25 Claims, No Drawings

CANDLES CAPABLE OF DIFFUSING A PLURALITY OF ACTIVE VOLATILE SUBSTANCES SIMULTANEOUSLY

TECHNICAL FIELD

The present invention relates to candles capable of diffusing a plurality of volatile active substances simultaneously comprising a base portion, at least one wick and a plurality of cartridges carrying the volatile active substances to be diffused, the base portion being provided with a plurality of holes adapted to receive the cartridges. The invention further relates to a method for diffusing a plurality of active substances simultaneously comprising manufacturing and burning such candle.

PRIOR ART

Several types of candles are described to be capable of diffusing an active substance into the surrounding area upon burning. In particular perfumed candles are described. Candles capable of diffusing a plurality of fragrances are also known. Such candles are made of several successive layers, each layer comprising a different type of perfume and often having a different color. However, these candles do not enable the diffusion of the plurality of fragrances at the same time, because each fragrance is diffused in turn, depending on the layer that is burning.

It would therefore be desirable to provide candles which are capable of diffusing a plurality of volatile active substances at the same time. It would also be desirable to provide candles which enable the consumer to select and combine the fragrances that will be diffused by the candle according to his desires. It would also be advantageous to provide perfumed candles capable of efficiently diffusing high loads of a plurality of fragrances while keeping the manufacturing costs at a low level. Such candles must also retain good burning properties. The present invention addresses and solves these problems.

DETAILED DESCRIPTION OF THE INVENTION

The present inventor has solved the above mentioned problems by providing a candle capable of diffusing a plurality of volatile active substances simultaneously comprising a base portion, at least one wick and a plurality of cartridges each carrying at least one volatile active substance, said base portion being provided with a plurality of holes adapted to receive said cartridges in an essentially vertical position relative to the base portion, the diameter of the cartridges being comprised between 0.2 inch (0.5 cm) and 2 inches (5.1 cm) and the diameter of the base portion being comprised between 0.5 inch (1.3 cm) and 12 inches (30.5 cm).

In a preferred embodiment of the invention, the candle comprises two or three cartridges and most preferably three cartridges.

In any embodiment of the invention, the volatile active substance carried by each cartridge may be identical or different. Preferably, the volatile active substance carried by at least one of the cartridges is different from the volatile active substance carried by the other cartridges. Most preferably, each cartridge carries a different active volatile substance.

The cartridges may be inserted in the base portion or may be provided separately and inserted in the base portion by the consumer before burning the candle. This allows the consumer to select the cartridges according to the desired result to achieve and to combine cartridges comprising diverse types of volatile active substances according to his needs.

The wick may be part of the cartridges and/or part of the base portion. In the case where more than one wick is present, the wicks are preferably at least 1 inch (2.5 cm) apart from each other. The at least one wick can be formed of any wicking material known to the person skilled in the art. Examples of preferred wicks are those containing a paper core, which have been observed to provide the most desired combination of burn characteristics, especially with respect to attributes such as smoke, bloom, fragrance throw and burn rate. However, other types of suitable wicks known to those skilled in the art, may also be used in accordance with the present invention. Non-limiting examples of suitable wicks and wicking materials are commercially available from Atkins-Pearce of Covington, Ky., USA.

In a preferred embodiment, the distance between the centre of each hole and the centre of the neighbouring holes is comprised between ⅓ and ½ times the diameter of the base portion. For example, for a base portion having a diameter of 3 inches (7.6 cm), the distance between the centre of each hole and the center of the neighbouring holes is comprised between 1 inch (2.5 cm) and 1.5 inch (3.8 cm). This has the advantage of providing good pooling of candle (i.e. optimal size and shape of the melted zone) and hence provides good diffusion and impact of the volatile active substance.

In a preferred embodiment of the invention, the length of the cartridges is comprised between 0.5 inch (1.3 cm) and 12 inches (30.5 cm).

In another preferred embodiment, the diameter of the holes and cartridges is comprised between 1/15 and ⅓ times the diameter of the base portion.

In another preferred embodiment, the base portion has exactly three holes which are positioned so that the centers of the three holes form a triangle which is essentially equilateral. The triangle is considered as essentially equilateral if each angle of the triangle is comprised between 55 and 65 degrees, preferably each angle is comprised between 58 and 62 degrees, most preferably each angle is 60 degrees. Such design is particularly advantageous when each cartridge comprises a wick, to prevent overlapping of the flame and flaring. Even when the wick is part of the base portion, such position of the holes and cartridges has the advantage of providing a pooling (i.e. a size and shape of the melted zone) enabling an improved diffusion of the volatile active substance.

In another preferred embodiment, the holes are positioned so that the center of each hole is at least 0.5 inch (1.3 cm), more preferably at least 0.75 inch (1.9 cm) away from the periphery of the base portion. This embodiment is particularly preferred when each cartridge comprises a wick to avoid dripping of pillar candles or excessive heating of the container in the case of container candles.

The active substance carried by the cartridges may be any type of volatile active substance. Preferably, it is a perfume, a malodour counteractant, an antibacterial agent, an insect repellent or any combination thereof. More preferably, it is a perfume, a malodour counteractant or a mixture thereof and most preferably a perfume.

For the purpose of the present invention, a “perfume” is meant as including any perfuming ingredient or a mixture thereof. A “perfuming ingredient” is meant here as a compound which is of current use in the perfumery industry, i.e. a compound which is used as active ingredient in perfumed candles in order to impart a hedonic effect into its surrounding. In other words, such an ingredient or mixture, to be considered as being a perfuming one, must be recognized by a person skilled in the art of perfumery as being able to impart or modify in a positive or pleasant way the odor of a candle, and not just as having an odor. Moreover, this definition is also meant to include compounds that do not necessarily have an odor but are capable of modulating the odor of a perfuming composition and, as a result, of modifying the perception by a user of the odor of such a composition.

The nature and type of these perfuming ingredients do not warrant a more detailed description here, which in any case would not be exhaustive, the skilled person being able to select them on the basis of his general knowledge, the intended use or application and the desired organoleptic effect. In general terms, these perfuming ingredients belong to chemical classes as varied as alcohols, aldehydes, ketones, esters, ethers, acetates, nitriles, terpene hydrocarbons, nitrogenous or sulphurous heterocyclic compounds and essential oils, and said perfuming ingredients can be of natural or synthetic origin. Many of these ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said ingredients may also be compounds known to release in a controlled manner various types of perfuming compounds.

By the term "malodor counteractant" or "malodor counteracting ingredient" we mean here compounds which are capable of reducing the perception of malodor, i.e. of an odor that is unpleasant or offensive to the human nose by counteracting and/or masking malodors. In a particular embodiment, these compounds have the ability to react with key compounds causing known malodors. The reactions result in reduction of the malodor materials' airborne levels and consequent reduction in the perception of the malodor.

Non-limiting examples of suitable insect repellants include citronella, dimethyl phthalate and n,n-dimethyl-m-tolumide.

The volatile active substance is typically present in an amount comprised between 10 and 25% by weight, based on the total weight of the cartridge.

The wax of the cartridges typically comprises mixture of paraffin, soy wax and polyolefin wax or, alternatively, ditrimethylol propane. In the first alternative, the wax preferably comprises between 60 and 80% of paraffin, between 6 and 10% of soy wax and between 1 and 6% of polyolefin wax. In the second alternative, the wax is preferably one of those disclosed in EP 1749080.

Typically, the polyolefin wax is a hyperbranched polymer formed by the polymerization of alpha olefins. The use of such a polyolefin wax has the advantage of hardening the cartridges' wax and of improving the ability of the wax to bind oil, thus enabling the cartridges to incorporate high levels of volatile active substance, in particular perfumes. An example of a particularly appreciated polyolefin wax is that sold under the trade name Vybar® 260 by Baker Petrolite.

The use of paraffin wax has beneficial effects on the surface texture of the cartridges, which appear smooth without blemishes. Examples of suitable paraffin wax include those sold under the trade names Paravan® 1300 and Paravan® 1270, which are commercially available by Exxon Mobile.

The wax of the base portion may be any kind of wax known to the person skilled in the art. It can be made of the same wax as the cartridges or of a different wax. In a preferred embodiment, said wax comprises paraffin or a wax of natural origin such as soy wax or beeswax or a mixture thereof. Blends of soy wax and fully or partially refined paraffin waxes are particularly preferred components of the wax of the base portion. Preferably, the soy wax is fully hydrogenated.

In a preferred embodiment, the base portion also comprises an active volatile substance, preferably a perfume.

The cartridge and the base portion may further comprise additional optional ingredients to provide enhanced or additional aesthetic and/or functional improvements. In particular, the additional materials that may be included in the wax include coloring agents, decorative materials, solvents, stabilizers, antioxidants, and UV blockers. Such optional ingredients do not warrant a more detailed description here, which would in any case not be exhaustive. The skilled person is capable to select them on the basis of his general knowledge and the desired characteristics of the candle. In particular, the kind and amount of the additional ingredients are selected among those that do not alter the structure or the burning properties of the cartridges or of the base portion.

The base portion may be a pillar candle or a container candle. When the candle is a container candle, it preferably has one or more of the following physical properties: a melting point comprised between 125° F. (51.7° C.) and 130° F. (54.4° C.), a needle penetration point of at most 17 mm, as measured using the ASTM D1321 method at 77° F. (25° C.) and an oil content of at most 0.2% by weight, relative to the total weight of the base portion. When the candle is a pillar candle, it preferably has one or more of the following physical properties: a melting point comprised between 135° F. (57.2° C.) and 140° F. (60° C.), a needle penetration point at of at most 12 mm, preferably at most 10 mm, as measured using the ASTM D1321 method at 77° F. (25° C.) and an oil content of at most 0.5% by weight, relative to the total weight of the base portion.

When the base portion is a pillar candle, it is further preferred that the wax of the base portion is of the same type as the wax of the cartridges, as defined in any of the above-described embodiments.

Upon melting, the cartridges may form separate pools of melted wax without overlap, so that the melted pools do not mix with each other or, alternatively the cartridges and the base portion may melt so as to form one single pool of melted wax. The latter is preferred when a particularly intense diffusion of the volatile active substance is desired. However, separate pools for each cartridge are preferred when it is desired to keep the opportunity of diffusing the volatile active substance of one or two of the cartridges independently of the others by burning some of the cartridges only, depending on the circumstances. In such a case, each cartridge preferably has a wick. For the purpose of the present invention, it is preferred that one single pool of melted wax is formed to enhance the active substance diffusion.

The size of the melted pool can be determined by the person skilled in the art on the basis of his general knowledge of the candles art by varying the wick size and/or the melting point and hardness of the wax.

In another embodiment, the invention provides a method for diffusing a plurality of volatile active substances comprising the following subsequent steps:

a) manufacturing a candle as described in any of the above embodiments; and b) burning the candle thus obtained.

The candle is manufactured using common methods in the art of making candles. For example, the components of the wax are mixed with each other, then the wax is heated to a temperature sufficient to enable shaping of the candle, such as moulding or pouring into a container. More details of processes that can be used to make the candles of the present invention are provided in the Examples below.

EXAMPLES

Example 1

Preparation of a Candle According to the Invention

A base portion was prepared using a wax comprising a mixture of soy wax and paraffin. The wax was heated to 170° F. (76.7° C.), poured into a mould and the base portion was cooled down to room temperature to form a cylindrical candle having a diameter of 3 inches (7.6 cm) and a height of 6 inches (15.2 cm).

Three holes were then drilled in the base portion thus formed. The holes had a diameter of 0.5 inch (1.3 cm) and a depth of 4 inches (10.2 cm). The holes were placed so that the centre of each hole was at a distance of 1 inch (2.5 cm) from the centre of the neighbouring holes. The centre of each hole was also at a distance of 0.5 inch (1.3 cm) from the periphery of the base portion.

Three cartridges were prepared with a wax having the following ingredients, in the amounts indicated.

TABLE 1 composition of the wax of the cartridges

| Ingredient | Amount (%) |
|---|---|
| Paravan ® 1300 MP 135-140[1)] | 76.0 |
| Vybar ® 260[2)] | 4.0 |
| Soy C300[3)] | 10.0 |
| Perfume[4)] | 10 |

[1)]Paraffin wax, origin: Exxon Mobile

[2)]Polyolefin wax, origin: Baker Petrolite

[3)]Soy wax, origin: Cargill.

[4)]The three cartridges were produced separately, each with one of the following perfumes: a perfume having a mango margarita character (n° 478168KW), a perfume having a honeysuckle character (n° 458452) and a perfume having a pina colada character (n° 299475), all available from Firmenich SA, Geneva, Switzerland.

The paraffin wax, polyolefin wax and soy wax were heated to 175° F. (79.4° C.) and well mixed. The fragrance was then admixed to the heated wax. The perfumed wax was then poured into a mould.

The physical properties of the cartridges were then determined. The needle penetration, as measured using the ASTM D1321 method at 25° C., was of 20 mm. The melting point was of 130° F. (54.4° C.).

The cartridges were then inserted into the holes of the base portion prepared above.

Example 2

Preparation of a Candle According to the Invention

A base portion was prepared using a wax comprising a mixture of soy wax and paraffin. The wax was heated to 170° F. (76.7° C.), poured into a mould and the base portion was cooled down to room temperature to form a cylindrical candle having a diameter of 3 inches (7.6 cm) and a height of 6 inches (15.2 cm).

Three holes were then drilled in the base portion thus formed. The holes had a diameter of 0.5 inch (1.3 cm) and a depth of 4 inches (10.2 cm). The holes were placed so that the periphery of each hole was at a distance of 1 inch (2.5 cm) from the centre of the other holes. The centre of each hole was also at a distance of 0.5 inch (1.3 cm) from the periphery of the base portion.

Three cartridges were prepared with a wax having the following ingredients, in the amounts indicated.

TABLE 2 composition of the wax of the cartridges

| Ingredient | Amount (%) |
|---|---|
| Paravan ® 1270 wax MP 135-140[1)] | 74.0 |
| Vybar ® 260[2)] | 5.0 |
| Soy C300[3)] | 6.0 |
| Fragrance[4)] | 15 |

[1)]Paraffin oil, origin: Exxon Mobile

[2)]Polyolefin wax, origin: Baker Petrolite

[3)]Soy wax, origin: Cargill

[4)]The three cartridges were produced separately, each with one of the following perfumes: a perfume having a mango margarita character (n° 478168KW), a perfume having a honeysuckle character (n° 458452) and a perfume having a pina colada character (n° 299475), all available from Firmenich SA, Geneva, Switzerland.

The paraffin wax, polyolefin wax and soy wax were heated to 175° F. (79.4° C.) and well mixed. The fragrance was then admixed to the heated wax. The perfumed wax was then poured into a mould.

The physical properties of the cartridges were then determined. The needle penetration, as measured using the ASTM D1321 method at 25° C., was of 20 mm. The melting point was of 130° F. (54.4° C.).

The cartridges were then inserted into the holes of the base portion prepared above.

The invention claimed is:

1. A candle capable of diffusing a plurality of volatile active substances simultaneously comprising a base portion, at least one wick and a plurality of user-selectable cartridges each carrying at least one volatile active substance, with the base portion provided with a plurality of holes for receiving the selected cartridges in an essentially vertical position relative to the base portion, the diameter of the cartridges being comprised between 0.2 and 2 inches and the diameter of the base portion being comprised between 0.5 and 12 inches.

2. A candle according to claim 1, wherein each cartridge carries a different volatile active substance.

3. A candle according to claim 1, comprising three cartridges.

4. A candle according to claim 1, wherein the distance between the centre of each hole and the centre of the neighbouring holes is comprised between ⅓ and ½ times the diameter of the base portion.

5. A candle according to claim 4, wherein the diameter of the holes and cartridges is comprised between 1/15 and ⅓ times the diameter of the base portion.

6. A candle according to claim 1, wherein the base portion is provided with three holes which are positioned so that the centres of the holes form a triangle which is essentially equilateral.

7. A candle according to claim 6, wherein each angle of the triangle is comprised between 55 and 65 degrees.

8. A candle according to claim 1, wherein the holes are positioned so that the centre of each hole is at least 0.5 inch away from the periphery of the base portion.

9. A candle according to claim 1, wherein the volatile active substance of each user-selectable cartridge is a perfume, a malodour counteractant, an antibacterial agent, an insect repellent or any combination thereof.

10. A candle according to claim 9, wherein the volatile active substance of each user-selectable cartridge is a perfume and the cartridges contain different perfumes.

11. A candle according to claim 1, wherein the volatile active substance in each user-selectable cartridge is present in an amount comprised between 10 and 25% by weight, based on the total weight of the cartridges.

12. A candle according claim 1, wherein the wax of the cartridges comprises a) a mixture of paraffin, soy wax and a polyolefin wax; or b) ditrimethylolpropane tetrastearate.

13. A candle according to claim 1, wherein the wax of the base portion comprises paraffin, soy wax, beeswax, or another wax of natural origin or a mixture thereof.

14. A method for diffusing a plurality of volatile active substances simultaneously comprising:

a) manufacturing a candle comprising a base portion, at least one wick and a plurality of user-selected cartridges each carrying at least one volatile active substance, with the base portion provided with a plurality of holes for receiving the selected cartridges in an essentially vertical position relative to the base portion, the diameter of the cartridges being comprised between 0.2 and 2 inches and the diameter of the base portion being comprised between 0.5 and 12 inches; and b) burning the candle thus obtained.

15. The method as recited in claim 14, wherein each cartridge carries a different volatile active substance.

16. The method as recited in claim 14, comprising three cartridges.

17. The method as recited in claim 14, wherein the distance between the centre of each hole and the centre of the neighbouring holes is comprised between ⅓ and ½ times the diameter of the base portion.

18. The method as recited in claim 14, wherein the diameter of the holes and cartridges is comprised between 1/15 and ⅓ times the diameter of the base portion.

19. The method as recited in 14, wherein the base portion is provided with three holes which are positioned so that the centres of the holes form a triangle which is essentially equilateral.

20. The method as recited in claim 19, wherein each angle of the triangle is comprised between 55 and 65 degrees.

21. The method as recited in claim 14, wherein the holes are positioned so that the centre of each hole is at least 0.5 inch away from the periphery of the base portion.

22. The method as recited in 14, wherein the volatile active substance of each user-selectable cartridge is a perfume, a malodour counteractant, an antibacterial agent, an insect repellent or any combination thereof.

23. The method as recited in claim 22, wherein the volatile active substance of each user-selectable cartridge is a perfume and the cartridges contain different perfumes.

24. The method as recited in claim 14, wherein the volatile active substance in each user-selectable cartridge is present in an amount comprised between 10 and 25% by weight, based on the total weight of the cartridges.

25. The method as recited in claim 14, wherein the wax of the cartridges comprises a) a mixture of paraffin, soy wax and a polyolefin wax; or b) ditrimethylolpropane tetrastearate.

* * * * *